(12) United States Patent
Pomper et al.

(10) Patent No.: US 7,408,079 B2
(45) Date of Patent: Aug. 5, 2008

(54) IMAGING AGENTS AND METHODS OF IMAGING NAALADASE OR PSMA

(75) Inventors: Martin Gilbert Pomper, Baltimore, MD (US); Jiazhong Zhang, Washington, DC (US); Alan P. Kozikowski, Princeton, NJ (US); John L. Musachio, Lutherville, MD (US)

(73) Assignee: The Johns Hopkins University, Baltimore, MD (US)

( * ) Notice: Subject to any disclaimer, the term of this patent is extended or adjusted under 35 U.S.C. 154(b) by 429 days.

(21) Appl. No.: 10/340,864

(22) Filed: Jan. 10, 2003

(65) Prior Publication Data
US 2004/0054190 A1 Mar. 18, 2004

Related U.S. Application Data

(60) Provisional application No. 60/347,487, filed on Jan. 10, 2002.

(51) Int. Cl.
*C07C 241/00* (2006.01)
*C07C 57/30* (2006.01)
*C07C 229/00* (2006.01)

(52) U.S. Cl. .................. 562/560; 562/439; 562/496; 560/34; 560/171

(58) Field of Classification Search ............ 564/58, 564/59, 60, 32, 47, 56; 560/155, 169, 171, 560/173; 562/553, 561, 571
See application file for complete search history.

(56) References Cited

U.S. PATENT DOCUMENTS 6,479,470 B1 * 11/2002 Kozikowski et al. .......... 514/75
6,528,499 B1 * 3/2003 Kozikowski et al. .......... 514/75

FOREIGN PATENT DOCUMENTS

| EP | 1 046 627 | 10/2000 |
| WO | WO 98/45256 | 10/1998 |
| WO | WO 00/64911 | 11/2000 |
| WO | WO 01/72958 | 10/2001 |
| WO | WO 02/22627 | 3/2002 |

OTHER PUBLICATIONS

Konda et al., "First total synthesis of Mer-N5075A and a diastereomeric mixture of α and β-MAPI, new HIV-I protease inhibitors from a species of *Streptomyces*," *Tetrahedron* 57:4311-4321 (2001).

(Continued)

*Primary Examiner*—Karl J Puttlitz
(74) *Attorney, Agent, or Firm*—Edwards Angell Palmer & Dodge LLP; Peter F. Corless; Jonathan M. Sparks

(57) ABSTRACT

The present invention relates to compounds particularly asymmetric urea compounds which are labeled with one or more radioisotopes and which are suitable for imaging or therapeutic treatment of tissues, organs, or tumors which express NAALADase and/or PSMA. In another embodiment, the invention relates to methods of imaging tissues, organs, or tumors using radiolabeled compounds of the invention, particularly tissues, organs, or tumors which express NAALADase and/or PSMA to which the compounds of the invention have an affinity.

28 Claims, 4 Drawing Sheets

OTHER PUBLICATIONS

Kozikowski et al., "Design of Remarkably Simple, Yet Potent Urea-Based Inhibitors of Glutamate Carboxypeptidase II (NAALADase)," *J. Med. Chem.*, 44:298-301 (2001).

Peter et al., "Application of (S)-*N*-(4-Nitrophenoxycarbonyl) phenylalanine Methoxyethyl Ester as a New Chiral Derivatizing Agent for Proteinogenic Amino Acid Analysis by High-Performance Liquid Chromatography," *Chromatogrphia* 52:821-826 (2000).

Pomper et al., "[11]C-MCG: Synthesis, Uptake Selectivity and Primate PET of a Probe for Glutamate Carboxypeptidase II (NAALADase)," *Molecular Imaging* 1:96-101 (2002).

Shin-Watanabe et al., "The Structure of β-MAPI, a Novel Proteinase Inhibitor," *Tetrahedron* 38:1775-1780 (1982).

Umezawa et al., "Structure of Antipain, a new Sakagushi-positive product of streptomyces," *Journal of Antibiotics* 25:267-270 (1972).

* cited by examiner

IMAGING AGENTS AND METHODS OF IMAGING NAALADASE OR PSMA

This application claims the benefit of U.S. Provisional Application Ser. No. 60/347,487 filed Jan. 10, 2002, the teachings of which are incorporated herein by reference.

This invention was supported by National Institute of Health (NIH) Grant No. CA92871. The United States government has certain rights to the invention.

BACKGROUND OF THE INVENTION

1. Field of the Invention

The present invention provides novel asymmetric urea compounds, particularly asymmetric urea compounds capable of binding with high selectivity and/or high affinity to N-Acylated alpha-linked L-amino dipeptidaase (NAALADase) (also known as glutamate carboxypeptidase II; GCP II) and/or prostate specific membrane antigen (PSMA). This invention also provides pharmaceutical compositions comprising such urea compounds. Additionally this invention provides imaging methods for localizing NAALADase and/or PSMA in tissues or cells using radiolabeled asymmetric urea compounds of the invention. The invention further provides treatment methods comprising administration of a high energy radiolabeled asymmetric urea to a patient, particularly patients suffering from prostate cancer.

2. Background

In the brain, the metalloprotease, glutamate carboxypeptidase II (GCP II; EC 3.4.17.21) cleaves N-acetyl-aspartyl-glutamate (NAAG) to N-acetyl-aspartate (NAA) and glutamate. The roles of GCP II in the brain are to terminate the neurotransmitter activity of NAAG and to produce glutamate that is then free to act as its various receptor subtypes.

GCP II and PSMA are very similar enzymes, such that an imaging probe for GCP II may serve useful to image PSMA. PSMA is expressed in a variety of normal and malignant tissues in and outside of the central nervous system (CNS). Immunohistochemistry using the anti-PSMA antibody 7E11-C5 has shown PSMA to have a fairly restricted pattern of expression in human tissues, with the highest levels of activity demonstrated in a subset of proximal renal tubules, prostate epithelium, and within the duodenum and colon. An immuno-cytochemical study that focused on the brain distribution of GCP II revealed staining of areas previously noted to contain immunoreactivity for NAAG, the natural substrate for GCP II. Those areas included the basal ganglia, hippocampus, substantia nigra, among others, and included regions that did not demonstrate NAAG immunoreactivity. A study that employed $^3$H-NAAG demonstrated a 14-fold elevation of PSMA in human prostate cancer relative to normal prostate tissue. PSMA expression is highest in high-grade and hormone-refractory disease. Using a panel of anti-PSMA antibodies, PSMA immunoreactivity has been demonstrated in tumor-associated neovasculature in a host of tumors, including breast, colon, and lung.

GCP II also possesses 87% sequence homology with the prostate-specific membrane antigen (PSMA). GCP II and PSMA exhibit some differences in substrate specificity and cellular localization. More particularly, GCP II has only a membrane bound form, whereas PSMA is found both in cell membranes and within cytosol. Notwithstanding the differences in substrate specificity and cellular localization, the enzymes have been shown to have similar pharmacological profiles.

Kozikowski et al recite a series of inhibitors of GCP II that maintain a structural motif similar to that of the phosphonic bis-dicarboxylic acid, 2-[(2,4-Dicarboxy-butyl)-hydroxy-phosphinoylmethyl]-pentanedioic acid, which is a potent inhibitor of GCP II, but has the central $CH_2P(O)(OH)CH_2$ group replaced with a urea group (J. Med. Chem. 2001 44: 298-301).

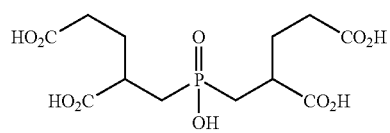

2-[(2,4-Dicarboxy-butyl)-hydroxy-phosphinoylmethyl]-pentanedioic acid

U.S. Pat. No 6,479,470 issued to Kozikowski reports a series of compounds according to the formula:

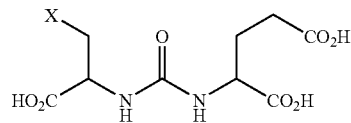

Where X is selected from —COOH, —C(O)NHOH, —C(O)NH$_2$, —C(S)SH, —SO$_3$H, —SO$_2$H, —SOH, —SeO$_3$H, —SeOH, —S(O)$_2$NH$_2$, —P(O)(OH)$_2$, and —P(OH)$_2$.

J. Frangioni teaches, in WO 02/098885 and WO 02/38190, a series of phosphonate, bisphosphonate and ester compounds and the use of same as imaging agents. Frangioni, in WO 01/72958, also teaches the use of various peptides in the diagnosis and treatment of diseases including bladder cancer.

mAb imaging and therapy for prostate cancer based on agents that bind either to intra- or extra-cellular domains of PSMA has been reported and includes Prostascint, a clinical agent that utilizes single photon emission computed tomography (SPECT) (Cancer Res. 1990, 50:6423-6429; Cancer Metastasis Rev. 1999, 18:483-490; and Cancer Res. 2000, 60:6095-6100).

It would be desirable to have a family of compounds, including radiolabeled compounds, having high affinity for GCP and/or PSMA, which can be readily prepared.

SUMMARY OF THE INVENTION

The invention provides novel asymmetric urea compounds of Formula I, and pharmaceutical compositions comprising compounds of Formula I and at least one pharmaceutically acceptable carrier or excipient. Preferred asymmetric urea compounds of the invention exhibit high affinity for at least one of NAALADase, i.e., GCP II, or PSMA.

The present invention provides asymmetric urea compounds according to Formula I

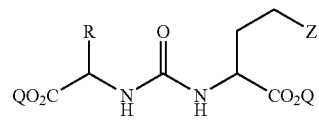

I wherein

R is selected from the group consisting of fluoroalky preferably having from 1 to 6 carbon atoms and about 1 and about 13 fluorine atoms, aryl, preferably having from 6 to about 12 carbon atoms and from 1 to 3 rings, benzyl, preferably having from 7 to 12 carbon atoms, thiol, and alkylthiol, preferably having from 1 to about 6 carbon atoms, each of which is optionally substituted with an optionally substituted alkyl, preferably having from 1 to about 6 carbon atoms, optionally substituted alkenyl, preferably having from 2 to about 6 carbon atoms, optionally substituted alkynyl, preferably having from 2 to about 6 carbon atoms, optionally substituted aryl, preferably having from 6 to about 12 carbon atoms in the ring and between about 1 and about 3 rings, optionally substituted alkanoyl, preferably having from 2 to about 6 carbon atoms, or optionally substituted aralky, preferably having from 7 to about 12 carbon atoms, optionally substituted alkoxy, preferably having from 1 to about 6 carbon atoms, optionally substituted aralkyloxy, preferably having from 7 to about 12 carbon atoms, or optionally substituted phenoxy, preferably having from about 6 to about 12 carbon atoms and from about 1 to about 3 rings;

Q is hydrogen, optionally substituted alkyl, optionally substituted benzyl or optionally substituted phenyl; and Z is Q or a tetrazole; or a pharmaceutically acceptable salt thereof.

The present invention provides asymmetric urea compounds of Formula I and subformula thereof which are substrates for the GCP II enzyme and are suitable for use in imaging or radiotherapeutic applications. The invention provides imaging agents comprising a radiolabeled or fluorescently labeled asymmetric urea of the invention which has one or more radioisotopes or fluorescent dyes which is capable of binding to GCP II. More particularly, the radiolabeled or fluorescently labeled asymmetric urea compounds of the invention are suitable for use in measuring GCP II activity in vivo under a variety of conditions wherein the radiation emitted by the radioisotope of the asymmetric urea is utilized to form the image. In preferred embodiments, radiolabeled asymmetric urea compounds of the invention comprise one or more radioisotopes capable of emitting positron radiation and are suitable for use in positron emission tomography (PET). Compounds of the invention are typically also suitable for binding to and imaging PSMA because of the high degree of sequence homology between GCP II and PSMA.

One class of asymmetric urea compounds provided by the present invention includes those ureas prepared by chemical modification of a carbonyl linked dipeptide selected from, Cys-C(O)-Glu, Phe-C(O)-Glu, or Tyr-C(O)-Glu where a one or more groups comprising a radioisotope have been coupled to the thiol group (Cys-C(O)-Glu) or the phenyl group (Phe/Tyr-C(O)-Glu). In an illustrative embodiment, Cys-C(O)-Glu was alkylated with $^{11}C$-iodomethane to form $^{11}C$-Me-Cys-C(O)-Glu ($^{11}C$-MCG; See Example 1). $^{11}C$-MCG exhibits high binding affinity for GCP II ($K_i = 1.9$ nM) and the $^{11}C$-MCG is selectively taken up in tissue expressing at least one of GCP II or PSMA.

According to yet another aspect, the present invention provides pharmaceutical compositions comprising radiolabeled or fluorescently labeled compounds of Formula I or the pharmaceutically acceptable salts or solvates thereof, which compositions are useful for the imaging of the above-recited enzymes, tissues expressing said enzymes, tumors or angiogenesis. The invention further provides methods of imaging patients suffering from any of the above-recited disorders or disorders with an effective amount of a compound or composition of the invention.

Additionally this invention relates to the use of the compounds of the invention (particularly labeled compounds of this invention emitting high energy radiation) as therapeutic agents for the treatment of diseases and disorders associated with elevated expression of enzymes for which the asymmetric urea compounds of the invention have high binding affinity, e.g., disorders or diseases associated with elevated MAALADase ro PSMA expression. Typical disease and disorders include cancer, tumors, stroke, collagen vascular disease, vascular malformations, normal tissue growth, and the like.

Preferred asymmetric urea compounds of the invention exhibit good binding activity and/or affinity for at least one of NAALADase and PSMA. Particularly preferred asymmetric urea compounds of the invention are GCP II inhibitors having a $K_i$ of about 1 micromolar or less, still more preferably a $K_i$ of about 100 nanomolar, 50 nanomolar or less or even more preferably a $K_i$ of about 10 nanomolar or less.

DETAILED DESCRIPTION OF THE INVENTION

Figure 1:
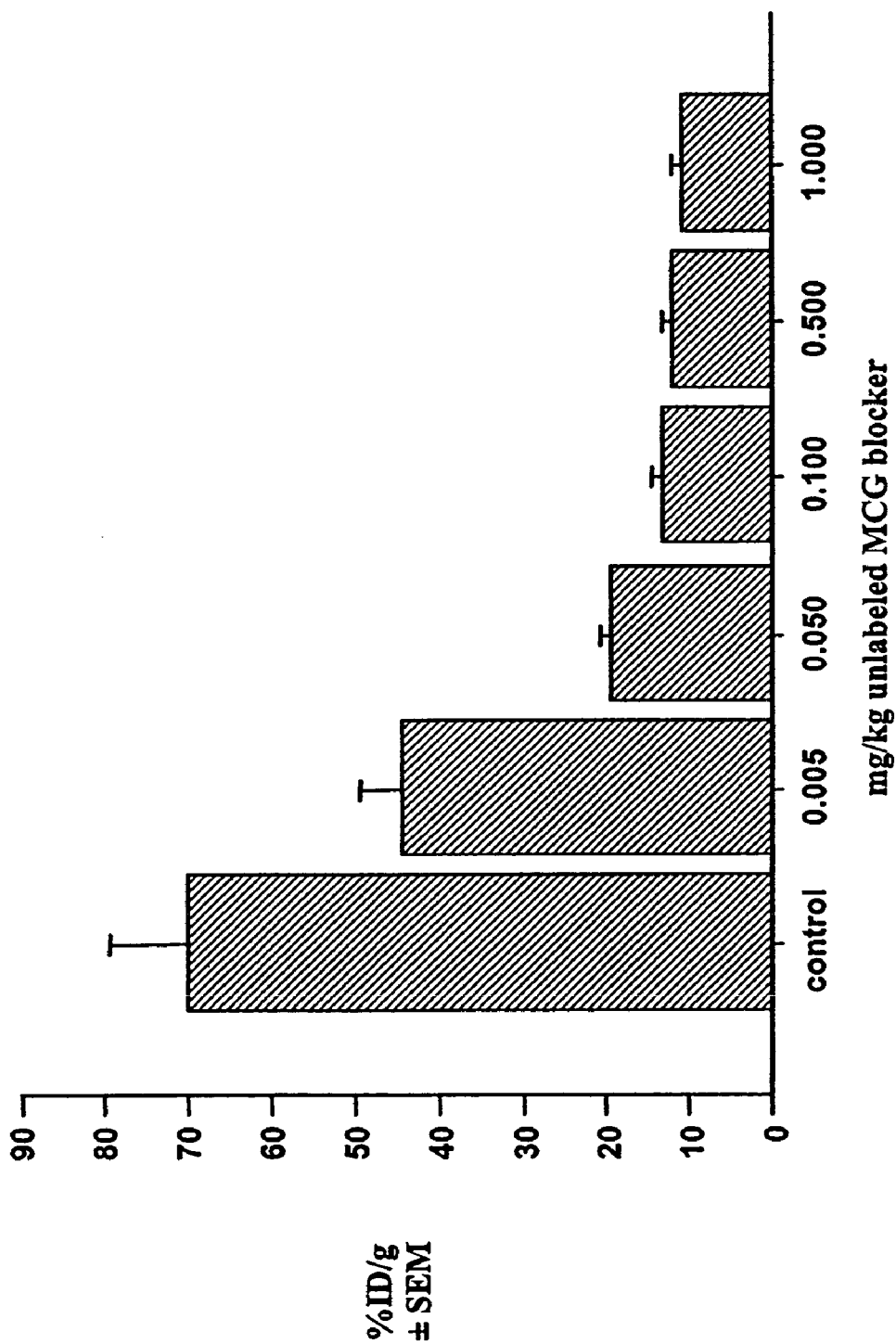
FIG. 1 is a table of the binding specificity of $^{11}C$-MCG to mouse kidney. Note decreasing $^{11}C$-MCG uptake (up to approximately seven fold) with increasing concentration of unlabeled MCG blocker. Uptake is expressed in percentage of injected dose per gram of tissue.

In addition to compounds of Formula I, described above, the invention is further directed to compounds and pharmaceutically acceptable salts of Formula I (shown above) wherein the compounds provided by the invention are compounds and salts of Formula IA.

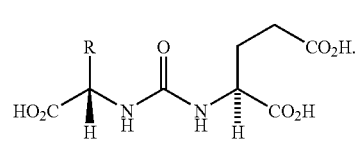

Ia

Other preferred asymmetric urea compounds provided by the invention include those compounds according to Formula II:

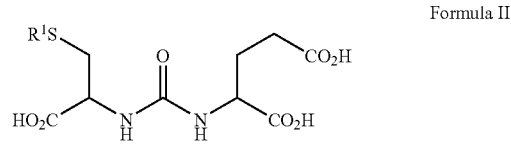

Formula II wherein $R^1$ is selected from optionally substituted alkyl, preferably having from 1 to about 6 carbon atoms, optionally substituted alkenyl, preferably having from 2 to about 6 carbon atoms, optionally substituted alkynyl, preferably having from 2 to about 6 carbon atoms, optionally substituted fluoroalkyl, preferably having from 1 to about 6 carbon atoms and between 1 and 2n+1 fluorine atoms (where n=number of carbon atoms), optionally substituted aryl, preferably having from about 6 to about 12 carbon atoms and between about 1 and about 3 rings, optionally substituted aralkyl, preferably having from 7 to about 12 carbon atoms; or a pharmaceutically acceptable salt thereof.

Yet other preferred asymmetric urea compounds provided by the invention include those compounds according to Formula III:

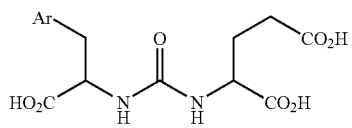

wherein Ar is a carbocyclic aromatic group having from 6 to about 18 carbon atoms and between 1 and about 3 rings which is substituted with one or more groups selected from halogen (including fluorine, chlorine, bromine, or iodine), optionally substituted alkyl, preferably having from 1 to about 6 carbon atoms, amino, hydroxy, optionally substituted alkenyl, preferably having from 2 to about 6 carbon atoms, optionally substituted alkynyl, preferably having from 2 to about 6 carbon atoms, optionally substituted benzoyloxy, preferably having between about 7 and about 12 carbon atoms, and optionally substituted alkoxy, preferably having from 1 to about 6 carbon atoms; or a pharmaceutically acceptable salt thereof.

Preferred compounds of Formula III include those compounds according to Formula IV:

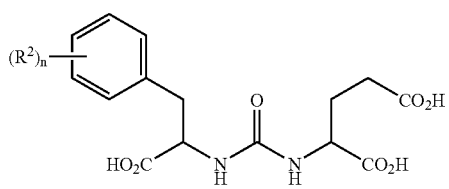

wherein $R^2$ is selected from the group consisting of fluoro, chloro, bromo, iodo, hydroxy, amino, mono and di alkylamino (where each alkyl preferably having from 1 to about 6 carbon atoms), optionally substituted alkyl, preferably having from 1 to about 6 carbon atoms, optionally substituted alkenyl, preferably having from 2 to about 6 carbon atoms, optionally substituted alkynyl, preferably having from 2 to about 6 carbon atoms, optionally substituted aryl, preferably having from about 6 to about 12 carbon atoms and between about 1 and about 3 rings, optionally substituted benzoyloxy, preferably having between about 7 and about 12 carbon atoms, and optionally substituted alkoxy, preferably having from 1 to about 6 carbon atoms; and n is an integer from about 1 to about 5.

Yet other preferred asymmetric urea compounds provided by the invention include those compounds according to Formula V:

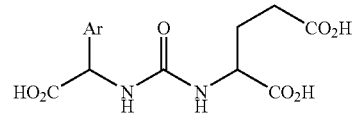

wherein Ar is a carbocyclic aromatic group having from 6 to about 18 carbon atoms and between 1 and about 3 rings which is substituted with one or more groups selected from halogen, alkyl, amino, hydroxy, optionally substituted alkyl, optionally substituted alkenyl, optionally substituted alkynyl, optionally substituted benzoyloxy, and optionally substituted alkoxy; or a pharmaceutically acceptable salt thereof.

Preferred compounds of Formula V include those compounds according to Formula VI:

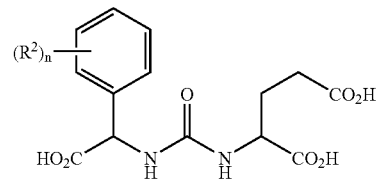

wherein $R^2$ is selected from the group consisting of fluoro, chloro, bromo, iodo, hydroxy, amino, mono and di alkylamino, optionally substituted alkyl, optionally substituted alkenyl, optionally substituted alkynyl, optionally substituted fluoroalkyl, optionally substituted aryl, optionally substituted benzoyloxy, and optionally substituted alkoxy; and n is an integer from about 1 to about 5.

Other preferred asymmetric urea compounds provided by the invention include those compounds according to Formula VII:

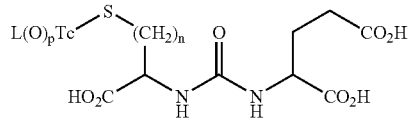

wherein

L is a chelating ligand suitable for coordination to Tc;

p is 0, or 1; and n is an integer of from about 1 to about 6; or a pharmaceutically acceptable salt thereof.

Preferred compounds of Formula VII include those compounds according to Formula VIII:

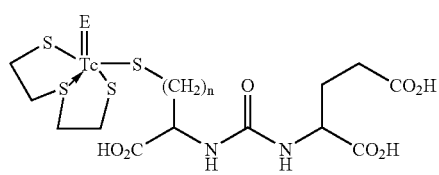

where E is oxygen or absent.

Additional preferred asymmetric urea compounds having a fluorescent dye include those compounds of Formula IV which are represented by Formula IX:

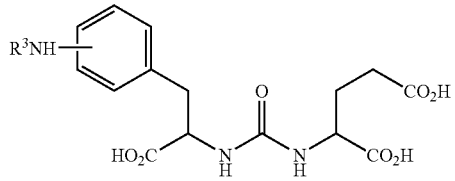

wherein $R^3$ is a fluorescent dye which emits in the visible or near infrared spectrum.

Particularly preferred compounds according to Formula IX include those compounds in which $R^3$ is FITC, a derivative thereof, carbocyanine, or a derivative thereof or other biocompatible dye capable of emitting sufficient radiation for detection and image acquisition.

Preferred compounds of the invention, particularly compounds suitable for use in the imaging methods provided by the invention, include one or more radioisotopes capable of emitting one or more forms of radiation which are suitable for detection with any standard radiology equipment such as PET, SPECT, gamma cameras, MRI and the like. Preferred radioisotopes include tritium and isotopes of carbon, fluorine, technetium, iodine and other isotopes capable of emitting positrons. Particularly preferred radioisotopes include $^{11}C$, $^{18}F$, $^{99}Tc$, and $^{123}I$.

Typically compounds of Formula II comprise a $R^1$ group having one or more radioisotopes. Particularly preferred $R^1$ groups include those selected from $^{11}C$-methyl, optionally substituted $C_{1-6}$alkyl, optionally substituted $C_{7-12}$aralkyl, optionally substituted $C_{6-12}$aryl, each of which may be substituted with one or more $^{11}C$-methyl groups, $^{18}F$, $^{99}Tc$, $^{123}I$, $^{125}I$, $^{131}I$, or a combination thereof.

Preferred compounds of Formula III and V comprise an Ar group having one or more substitutents which have a radioisotope included therein, e.g., compounds of Formula IV and VI typically comprise one or more $R^2$ groups having a radioisotope therein. Particularly preferred compounds of Formula IV and VI include those wherein $R^2$ is selected from the group consisting of $^{11}C$-methyl, $^{11}C$-methoxy, optionally substituted $C_{1-6}$alkyl, optionally substituted $C_{7-12}$aralkyl, optionally substituted $C_{6-12}$aryl, each of which may be substituted with one or more $^{11}C$-methyl groups, $^{18}F$, $^{99}Tc$, $^{123}I$, $^{125}I$, $^{131}$, or a combination thereof. Other particularly preferred compounds of Formula IV and VI include those wherein $R^2$ is selected from hydroxy, $^{11}C$-methoxy, $^{11}C$-methyl, $^{18}F$, $^{123}I$, $^{99}Tc$ coordination complexes, benzoyloxy which may be substituted with one or more fluoro groups, or a combination thereof.

Compounds of any one of Formula I, Ia, II, III, IV, V, VI, VII, VIII, of IX possess a binding affinity to at least one of NAALADase and/or PSMA of 10 micromolar or less, more preferably of 1 micromolar or less, 100 nanomolar or less, 50 nanomolar or less, 25 nanomolar or less, or most preferably of 10 nanomolar or less.

Particularly preferred compounds according to Formula I include the following non-limiting embodiments:

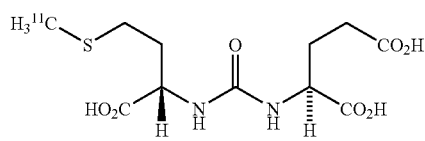

2-[3-(1-Carboxy-3-$^{11}$C-methylsulfanyl-propyl)-ureido]-pentanedioic acid

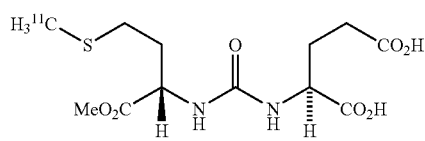

2-[3-(1-Methoxycarbonyl-3-methylsulfanyl-propyl)-ureido]-pentanedioic acid

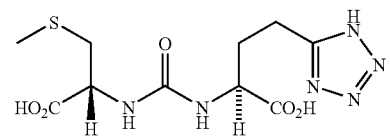

2-[3-(1-Carboxy-2-methylsulfanyl-ethyl)-ureido]-4-(1H-tetrazol-5-yl)-butyric acid

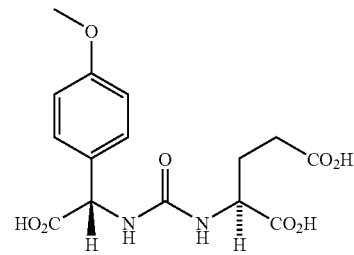

2-{3-[Carboxy-(4-methoxy-phenyl)-methyl]-ureido}-pentanedioic acid

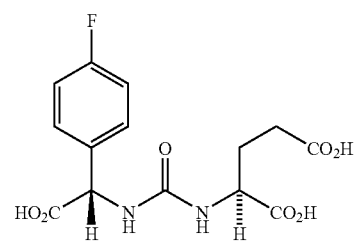

2-{3-[Carboxy-(4-fluoro-phenyl)-methyl]-ureido}-pentanedioic acid

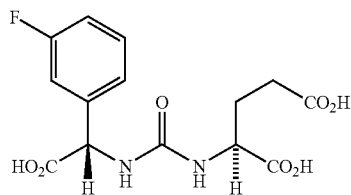

2-{3-[Carboxy-(3-fluoro-phenyl)-methyl]-ureido}-pentanedioic acid

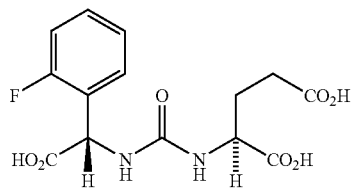

2-{3-[Carboxy-(2-fluoro-phenyl)-methyl]-ureido}-pentanedioic acid

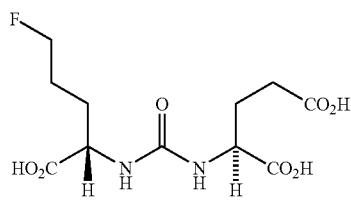

2-[3-(1-Carboxy-4-fluoro-butyl)-ureido]-pentanedioic acid

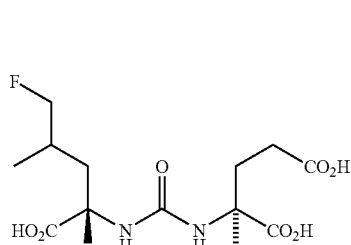

2-[3-(1-Carboxy-4-fluoro-3-methyl-butyl)-ureido]-pentanedioic acid

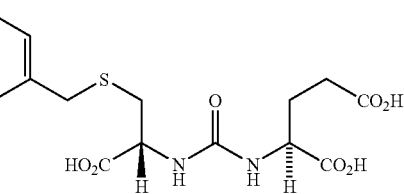

2-{3-[1-Carboxy-2-(2-fluoro-benzylsulfanyl)-ethyl]-ureido}-pentanedioic acid

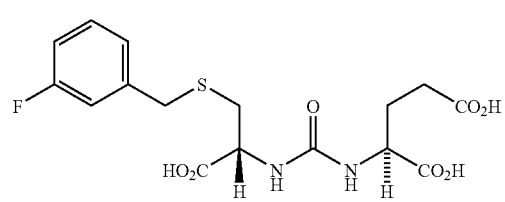

2-{3-[1-Carboxy-2-(3-fluoro-benzylsulfanyl)-ethyl]-ureido}-pentanedioic acid

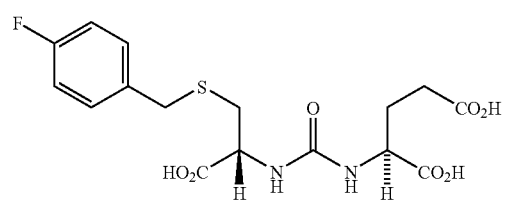

2-{3-[1-Carboxy-2-(4-fluoro-benzylsulfanyl)-ethyl]-ureido}-pentanedioic acid

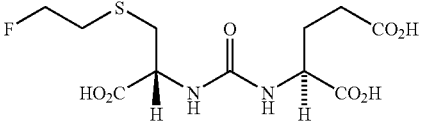

2-{3-[1-Carboxy-2-(2-fluoro-ethylsulfanyl)-ethyl]-ureido}-pentanedioic acid

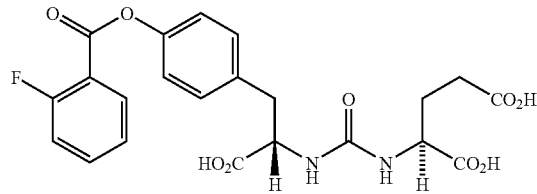

2-(3-{1-Carboxy-2-[4-(2-fluoro-benzoyloxy)-phenyl]-ethyl}-ureido)-pentanedioic acid

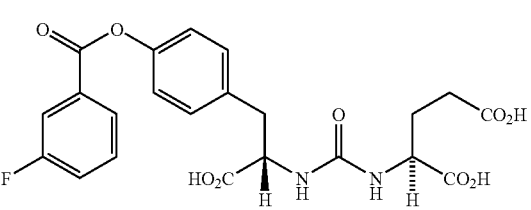

11

2-(3-{1-Carboxy-2-[4-(3-fluoro-benzoyloxy)-phenyl]-ethyl}-ureido)-pentanedioic acid

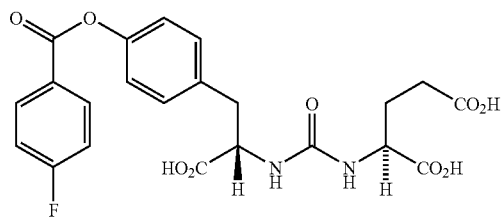

2-(3-{1-Carboxy-2-[4-(4-fluoro-benzoyloxy)-phenyl]-ethyl}-ureido)-pentanedioic acid

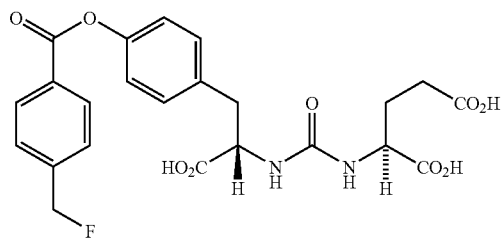

2-(3-{1-Carboxy-2-[4-(4-fluoromethyl-benzoyloxy)-phenyl]-ethyl}-ureido)-pentanedioic acid

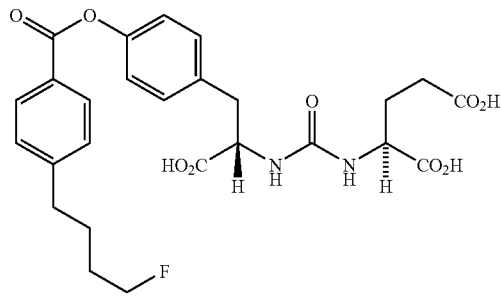

2-[3-(1-Carboxy-2-{4-[4-(4-fluoro-butyl)-benzoyloxy]-phenyl}-ethyl)-ureido]-pentanedioic acid

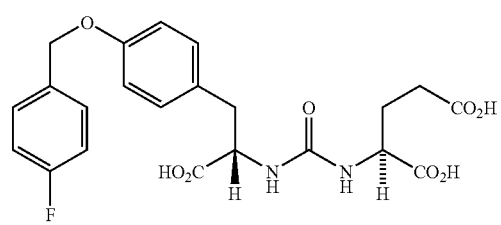

12

2-(3-{1-Carboxy-2-[4-(4-fluoro-benzyloxy)-phenyl]-ethyl}-ureido)-pentanedioic acid

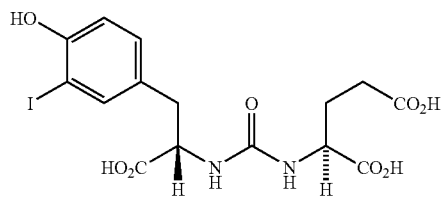

2-{3-[1-Carboxy-2-(4-hydroxy-3-iodo-phenyl)-ethyl]-ureido}-pentanedioic acid

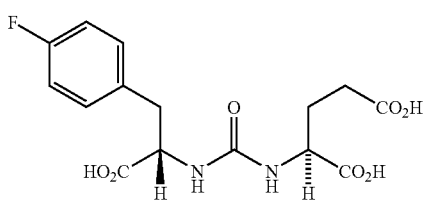

2-{3-[1-Carboxy-2-(4-fluoro-phenyl)-ethyl]-ureido}-pentanedioic acid

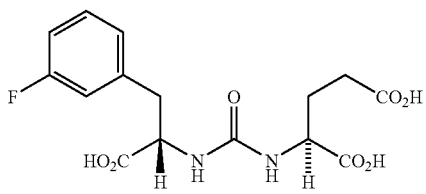

2-{3-[1-Carboxy-2-(3-fluoro-phenyl)-ethyl]-ureido}-pentanedioic acid

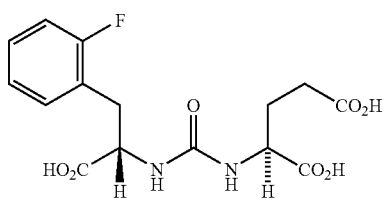

13

2-{3-[1-Carboxy-2-(2-fluoro-phenyl)-ethyl]-ureido}-
pentanedioic acid

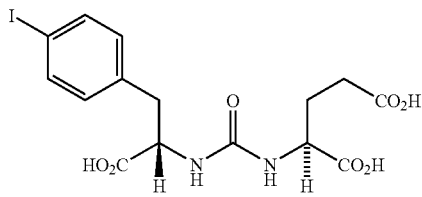

2-{3-[1-Carboxy-2-(4-Iodo-phenyl)-ethyl]-ureido}-
pentanedioic acid

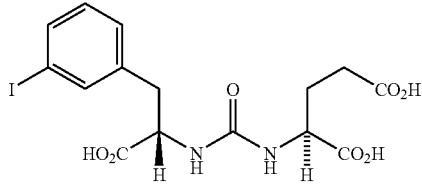

2-{3-[1-Carboxy-2-(3-iodo-phenyl)-ethyl]-ureido}-
pentanedioic acid

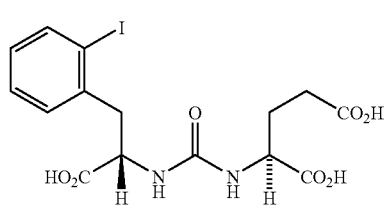

14

2-{3-[1-Carboxy-2-(2-iodo-phenyl)-ethyl]-ureido}-
pentanedioic acid

The present invention also provides technetium labeled complexes including the preferred complexes, as follows:

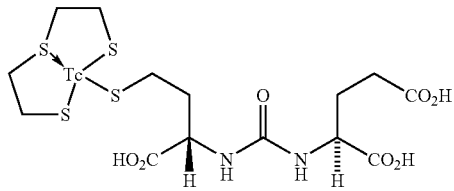

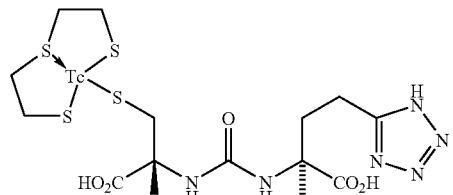

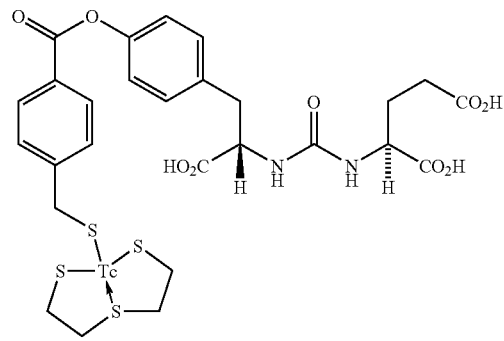

The present invention also provides fluorescently labeled compounds including the preferred fluorescent asymmetric ureas having FITC or carbocyanine, as follows:

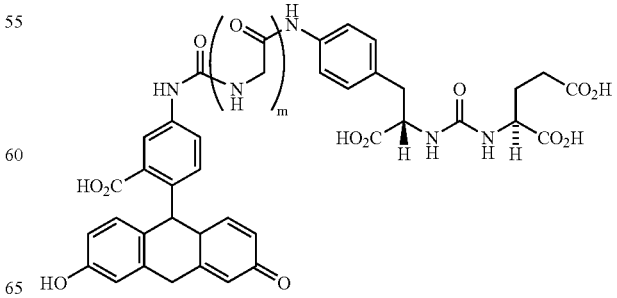

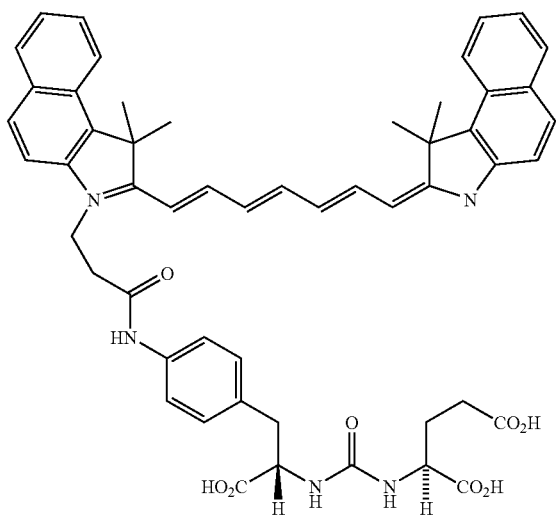

The present invention further provides method of imaging which comprise the steps of:

Providing at least one radiolabeled compound according to any one of Formula I, Ia, II, III, IV, V, VI, VII, VIII, of IX;

contacting cells or tissues with the radiolabeled compound; and making a radiographic image.

The imaging methods of the invention are suitable for imaging any physiological process or feature in which NAALADase or PSMA are involved. Typically, imaging methods ore suitable for identification of areas of tissues or targets which express high concentrations of NAALADase or PSMA. Preferred applications include imaging glutamateric neurotransmission, presynaptic glutamatergic neurotransmission, malignant tumors or cancer that express at least one of NAALADase or PSMA, prostate cancer (including metastasized prostate cancer), and angiogenesis.

The methods of imaging angiogenesis provided by the present invention are suitable for use in imaging a variety of diseases and disorders in which angiogenesis takes place. Illustrative, non-limiting, examples include tumors, collagen vascular disease, cancer, stroke, vascular malformations, retinopathy. Methods of imaging angiogenesis provided by the present invention are also suitable for use in diagnosis and observation of normal tissue development.

Preferred imaging methods provided by the invention include the use of compounds according to any one of Formula I, Ia, II, III, IV, V, VI, VII, VIII, of IX which are capable of generating at least a 2:1 target to background ratio of radiation intensity, or more preferably about a 5:1, about a 10:1 or about a 15:1 ratio of radiation intensity between target and background.

In preferred methods of the invention the compounds of the invention are excreted from tissues of the body quickly to prevent prolonged exposure to the radiation of the radiolabeled compound administered to the patient. Typically compounds according to Formula I or any subformula thereof are eliminated from the body in less than about 24 hours. More preferably, compounds of the invention are eliminated from the body in less than about 16 hours, 12 hours, 8 hours, 6 hours, 4 hours, 2 hours, 90 minutes, or 60 minutes. Typically preferred compounds are eliminated in between about 60 minutes and about 120 minutes.

Preferred compounds of the invention are stable in vivo such that substantially all, e.g., more than about 50%, 60%, 70%, 80%, or more preferably 90% of the injected compound is not metabolized by the body prior to excretion.

Compounds of the invention and imaging methods of the invention are useful in imaging a variety of conditions including presynaptic imaging of glutamatergic neurotransmission, identification of prostate tumors and metastasized prostate tumors, and imaging of angiogenesis. Methods of imaging angiogenesis provided by the present invention using radiolabeled asymmetric ureas are suitable for imaging angiogenesis associated with tumor growth, collagen vascular disease, stroke, vascular malformations, retinopathy and normal tissue development.

NAALADase and PSMA are frequently expressed in endothelial cells of capillary vessels in peritumoral and endotumoral areas of various malignancies such that compounds of the invention and methods of imaging using same are suitable for imaging such malignancies.

Typical subjects to which compounds of the invention may be administered will be mammals, particularly primates, especially humans. For veterinary applications, a wide variety of subjects will be suitable, e.g. livestock such as cattle, sheep, goats, cows, swine and the like; poultry such as chickens, ducks, geese, turkeys, and the like; and domesticated animals particularly pets such as dogs and cats. For diagnostic or research applications, a wide variety of mammals will be suitable subjects including rodents (e.g. mice, rats, hamsters), rabbits, primates, and swine such as inbred pigs and the like. Additionally, for in vitro applications, such as in vitro diagnostic and research applications, body fluids and cell samples of the above subjects will be suitable for use such as mammalian, particularly primate such as human, blood, urine or tissue samples, or blood urine or tissue samples of the animals mentioned for veterinary applications.

The present invention also provide packaged pharmaceutical compositions comprising a pharmaceutical acceptable carrier and a compound or salt of any one of Formula I, Ia, II, III, IV, V, VI, VII, VIII, of IX. In certain embodiments the packaged pharmaceutical composition will comprise the reaction precursors necessary generate the compound or salt according to Formula I or subformula thereof upon combination with a radiolabeled precursor. Other packaged pharmaceutical compositions provided by the present invention further comprise indicia comprising at least one of: instructions for using the composition to image cells or tissues expressing at least one of NAALADase or PSMA, or instructions for using the composition to image glutamatergic neurotransmission in a patient suffering from a stress-related disorder, or instructions for using the composition to image prostate cancer.

In certain preferred embodiments, the invention provides a kit according to the invention contains from about 1 to about 30 mCi of the radionuclide-labeled imaging agent described above, in combination with a pharmaceutically acceptable carrier. The imaging agent and carrier may be provided in solution or in lyophilized form. When the imaging agent and carrier of the kit are in lyophilized form, the kit may optionally contain a sterile and physiologically acceptable reconstitution medium such as water, saline, buffered saline, and the like.

In another embodiment, the kit of the invention may contain the targeting molecule which has been covalently or non-covalently combined with a chelating agent; an auxiliary molecule such as mannitol, gluconate, glucoheptonate, tartrate, and the like; and a reducing agent such as $SnCl_2$, Na dithionite or tin tartrate. The targeting molecule/chelating agent and the auxiliary molecule may be present as separate components of the kit or they may be combined into one kit component. The unlabeled targeting molecule/chelating agent, the auxiliary molecule, and the reducing agent may be provided in solution or in lyophilized form, and these components of the kit of the invention may optionally contain stabilizers such as NaCl, silicate, phosphate buffers, ascorbic acid, gentisic acid, and the like. Additional stabilization of kit components may be provided in this embodiment, for example, by providing the reducing agent in an oxidation-resistant form.

Determination and optimization of such stabilizers and stabilization methods are well within the level of skill in the art. When the targeting molecule/chelating agent of this embodiment are in lyophilized form, the kit may optionally contain a sterile and physiologically acceptable reconstitution medium such as water, saline, buffered saline, and the like. The amounts of unlabeled targeting molecule/chelating agent, auxiliary molecule, and reducing agent in this embodiment are optimized in accordance with the methods for making the cardiovascular imaging agent set forth above. Radionuclides, including, but not limited to, $^{99m}$Tc obtained from a commercially available $^{99}$Mo/$^{99m}$Tc generator or commercially available $^{123}$I, may be combined with the unlabeled targeting molecule/chelating agent and the reducing agent for a time and at a temperature sufficient to chelate the radionuclide to the targeting molecule/chelating agent, and the imaging agent thus formed is injected into the patient.

Imaging agents of the invention may be used in accordance with the methods of the invention by one of skill in the art, e.g., by specialists in nuclear medicine, to image sites having a high density of NAALADase or PSMA concentration in a subject or patient. Ay site of increased enzyme concentration may be imaged by the imaging methods and imaging agents of the present invention.

Images can be generated by virtue of differences in the spatial distribution of the imaging agents which accumulate at a site having a high density of NAALADase or PSMA. The spatial distribution may be measured using any means suitable for the particular label, for example, a gamma camera, a PET apparatus, a SPECT apparatus, and the like. The extent of accumulation of the imaging agent may be quantified using known methods for quantifying radioactive emissions. A particularly useful imaging approach employs more than one imaging agent to perform simultaneous studies.

Preferably, a detectably effective amount of the imaging agent of the invention is administered to a subject. In accordance with the invention, "a detectably effective amount" of the imaging agent of the invention is defined as an amount sufficient to yield an acceptable image using equipment which is available for clinical use. A detectably effective amount of the imaging agent of the invention may be administered in more than one injection. The detectably effective amount of the imaging agent of the invention can vary according to factors such as the degree of susceptibility of the individual, the age, sex, and weight of the individual, idiosyncratic responses of the individual, the dosimetry. Detectably effective amounts of the imaging agent of the invention can also vary according to instrument and film-related factors. Optimization of such factors is well within the level of skill in the art.

The amount of imaging agent used for diagnostic purposes and the duration of the imaging study will depend upon the radionuclide used to label the agent, the body mass of the patient, the nature and severity of the condition being treated, the nature of therapeutic treatments which the patient has undergone, and on the idiosyncratic responses of the patient. Ultimately, the attending physician will decide the amount of imaging agent to administer to each individual patient and the duration of the imaging study.

Chemical Description and Terminology

The compounds herein described may have one or more asymmetric centers or planes. Compounds of the present invention containing an asymmetrically substituted atom may be isolated in optically active or racemic forms. It is well known in the art how to prepare optically active forms, such as by resolution of racemic forms (racemates), by asymmetric synthesis, or by synthesis from optically active starting materials. Resolution of the racemates can be accomplished, for example, by conventional methods such as crystallization in the presence of a resolving agent, or chromatography, using, for example a chiral HPLC column. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

When any variable occurs more than one time in any constituent or formula for a compound, its definition at each occurrence is independent of its definition at every other occurrence. Thus, for example, if a group is shown to be substituted with 0-2 R*, then said group may optionally be substituted with up to two R* groups and R* at each occurrence is selected independently from the definition of R*. Also, combinations of substituents and/or variables are permissible only if such combinations result in stable compounds.

As indicated above, various substituents of the various formulae (compounds of Formula I, Ia, II, III, IV, V, VI, VII, VIII, of IX) are "optionally substituted", including Ar, R, $R^1$, $R^2$, $R^3$, Q, or Z of Formula I and subformulae thereof, and such substituents as recited in the sub-formulae such as Formula I and subformulae. The term "substituted," as used herein, means that any one or more hydrogens on the designated atom or group is replaced with a selection from the indicated group of substituents, provided that the designated atom's normal valence is not exceeded, and that the substitution results in a stable compound. When a substituent is oxo (keto, i.e., =O), then 2 hydrogens on an atom are replaced. The present invention is intended to include all isotopes (including radioisotopes) of atoms occurring in the present compounds.

When substituents such as Ar, R, $R^1$, $R^2$, $R^3$, Q, or Z of Formula I and subformulae thereof, and such substituents as recited in the sub-formulae are further substituted, they may be so substituted at one or more available positions, typically 1 to 3 or 4 positions, by one or more suitable groups such as those disclosed herein. Suitable groups that may be present on a "substituted" $R_1$, $R_2$, $R_3$ or other group include e.g., halogen; cyano; hydroxyl; nitro; azido; alkanoyl (such as a $C_{1-6}$ alkanoyl group such as acyl or the like); carboxamido; alkyl groups (including cycloalkyl groups, having 1 to about 8 carbon atoms, preferably 1, 2, 3, 4, 5, or 6 carbon atoms); alkenyl and alkynyl groups (including groups having one or more unsaturated linkages and from 2 to about 8, preferably 2, 3, 4, 5 or 6, carbon atoms); alkoxy groups having one or more oxygen linkages and from 1 to about 8, preferably 1, 2, 3, 4, 5 or 6 carbon atoms; aryloxy such as phenoxy; alkylthio groups including those having one or more thioether linkages and from 1 to about 8 carbon atoms, preferably 1, 2, 3, 4, 5 or 6 carbon atoms; alkylsulfinyl groups including those having one or more sulfinyl linkages and from 1 to about 8 carbon atoms, preferably 1, 2, 3, 4, 5, or 6 carbon atoms; alkylsulfonyl groups including those having one or more sulfonyl linkages and from 1 to about 8 carbon atoms, preferably 1, 2, 3, 4, 5, or 6 carbon atoms; aminoalkyl groups including groups having one or more N atoms and from 1 to about 8, preferably 1, 2, 3, 4, 5 or 6, carbon atoms; carbocyclic aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being a preferred arylalkyl group; arylalkoxy having 1 to 3 separate or fused rings and from 6 to about 18 ring carbon atoms, with O-benzyl being a preferred arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino.

As used herein, "alkyl" is intended to include both branched and straight-chain saturated aliphatic hydrocarbon groups, having the specified number of carbon atoms. Examples of alkyl include, but are not limited to, methyl, ethyl, n-propyl, i-propyl, n-butyl, s-butyl, t-butyl, n-pentyl, and s-pentyl. Preferred alkyl groups are $C_{1-6}$ alkyl groups. Especially preferred alkyl groups are methyl, ethyl, propyl, butyl, and 3-pentyl. The term $C_{1-4}$ alkyl as used herein includes alkyl groups consisting of 1 to 4 carbon atoms, which may contain a cyclopropyl moiety. Suitable examples are methyl, ethyl, and cyclopropylmethyl.

"Cycloalkyl" is intended to include saturated ring groups, having the specified number of carbon atoms, such as cyclopropyl, cyclobutyl, cyclopentyl, or cyclohexyl. Cycloalkyl groups typically will have 3 to about 8 ring members.

In the term "$(C_{3-8}$ cycloalkyl$)C_{1-4}$ alkyl", cycloalkyl, and alkyl are as defined above, and the point of attachment is on the alkyl group. This term encompasses, but is not limited to, cyclopropylmethyl, cyclohexylmethyl, and cyclohexylmethyl.

"Alkenyl" is intended to include hydrocarbon chains of either a straight or branched configuration comprising one or more unsaturated carbon-carbon bonds, which may occur in any stable point along the chain, such as ethenyl and propenyl. Alkenyl groups typically will have 2 to about 8 carbon atoms, more typically 2 to about 6 carbon atoms.

"Alkynyl" is intended to include hydrocarbon chains of either a straight or branched configuration comprising one or more carbon-carbon triple bonds, which may occur in any stable point along the chain, such as ethynyl and propynyl. Alkynyl groups typically will have 2 to about 8 carbon atoms, more typically 2 to about 6 carbon atoms.

"Haloalkyl" is intended to include both branched and straight-chain saturated aliphatic hydrocarbon groups having the specified number of carbon atoms, substituted with 1 or more halogen atoms. Examples of haloalkyl include, but are not limited to, mono-, di-, or tri-fluoromethyl, mono-, di-, or tri-chloromethyl, mono-, di-, tri-, tetra-, or penta-fluoro ethyl, and mono-, di-, tri-, tetra-, or penta-chloroethyl. Typical haloalkyl groups will have 1 to about 8 carbon atoms, more typically 1 to about 6 carbon atoms.

"Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Alkoxy groups typically have 1 to about 8 carbon atoms, more typically 1 to about 6 carbon atoms.

"Halolkoxy" represents a haloalkyl group as defined above with the indicated number of carbon atoms attached through an oxygen bridge.

As used herein, the term "alkylthio" includes those groups having one or more thioether linkages and preferably from 1 to about 8 carbon atoms, more typically 1 to about 6 carbon atoms.

As used herein, the term "alkylsulfinyl" includes those groups having one or more sulfoxide (SO) linkage groups and typically from 1 to about 8 carbon atoms, more typically 1 to about 6 carbon atoms.

As used herein, the term "alkylsulfonyl" includes those groups having one or more sulfonyl ($SO_2$) linkage groups and typically from 1 to about 8 carbon atoms, more typically 1 to about 6 carbon atoms.

As used herein, the term "alkylamino" includes those groups having one or more primary, secondary and/or tertiary amine groups and typically from 1 to about 8 carbon atoms, more typically 1 to about 6 carbon atoms.

"Halo" or "halogen" as used herein refers to fluoro, chloro, bromo, or iodo; and "counter-ion" is used to represent a small, negatively charged species such as chloride, bromide, hydroxide, acetate, sulfate, and the like.

As used herein, "carbocyclic group" is intended to mean any stable 3- to 7-membered monocyclic or bicyclic or 7- to 13-membered bicyclic or tricyclic group, any of which may be saturated, partially unsaturated, or aromatic. In addition to those exemplified elsewhere herein, examples of such carbocycles include, but are not limited to, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, and tetrahydronaphthyl.

As used herein, the term "heterocyclic group" is intended to include saturated, partially unsaturated, or unsaturated (aromatic) groups having 1 to 3 (preferably fused) rings with 3 to about 8 members per ring at least one ring containing an atom selected from N, O or S. The nitrogen and sulfur heteroatoms may optionally be oxidized. The term or "heterocycloalkyl" is used to refer to saturated heterocyclic groups.

The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. As used herein, the term "aromatic heterocyclic system" is intended to include any stable 5- to 7-membered monocyclic or 10- to 14-membered bicyclic heterocyclic aromatic ring system which comprises carbon atoms and from 1 to 4 heteroatoms independently selected from the group consisting of N, O and S. It is preferred that the total number of S and O atoms in the aromatic heterocycle is not more than 2, more preferably not more than 1.

Examples of heterocycles include, but are not limited to, those exemplified elsewhere herein and further include acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl;-1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred heterocyclic groups include, but are not limited to, pyridinyl, pyrimidinyl, furanyl, thienyl, pyrrolyl, pyrazolyl, pyrrolidinyl, morpholinyl, piperidinyl, piperazinyl, and imidazolyl. Also included are fused ring and spiro compounds containing, for example, the above heterocycles.

As used herein, the term "carbocyclic aryl" includes groups that contain 1 to 3 separate or fused rings and from 6 to about 18 ring atoms, without hetero atoms as ring members. Specifically preferred carbocyclic aryl groups include phenyl, and naphthyl including 1-napthyl and 2-naphthyl.

A "pharmaceutically acceptable carrier" refers to a biocompatible solution, having due regard to sterility, pH, isotonicity, stability, and the like and can include any and all solvents, diluents (including sterile saline, Sodium Chloride Injection, Ringer's Injection, Dextrose Injection, Dextrose and Sodium Chloride Injection, Lactated Ringer's Injection and other aqueous buffer solutions), dispersion media, coatings, antibacterial and antifungal agents, isotonic agents, and the like. The pharmaceutically acceptable carrier may also contain stabilizers, preservatives, antioxidants, or other additives, which are well known to one of skill in the art, or other vehicle as known in the art.

As used herein, "pharmaceutically acceptable salts" refer to derivatives of the disclosed compounds wherein the parent compound is modified by making non-toxic acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, malefic, hydroxymaleic, phenylacetic, glutamic, benzoic, salicylic, mesylic, sulfanilic, 2-acetoxybenzoic, fumaric, toluenesulfonic, methanesulfonic, ethane disulfonic, oxalic, isethionic, HOOC—(CH$_2$)n-COOH where n is 0-4, and the like. The pharmaceutically acceptable salts of the present invention can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts may be found, e.g., in *Remington's Pharmaceutical Sciences,* 17th ed., Mack Publishing Company, Easton, Pa., p. 1418 (1985).

Because of the distribution and variety of functions for GCP II, an imaging agent that can quantify GCP II activity is suitable for use in studying presynaptic glutamatergic transmission and diagnosis and monitoring of prostate cancer or tumor neoangiogenesis.

Because the rodent prostate does not demonstrate significant PSMA activity (ref 3) or [$^3$H]PMPA uptake, the kidney was used as a surrogate organ for the in vivo $^{11}$C-MCG uptake studies. The high level of $^{11}$C-MCG uptake, prompt washout during the 90 minute study (Table 1), and significant blockage of the active sites by pretreatment with a known high affinity GCP II inhibitor, e.g., unlabeled MCG or PMPA (FIGS. 1 and 2A respectively), suggest that $^{11}$C-MCG may be a site-selective imaging agent for GCP II.

Although not wishing to be bound by theory, $^{11}$C-MCG may also possess some nonspecific binding because there is no $^{11}$C-MCG uptake with blockade. That could be due to several factors, including the fact that the route of excretion of MCG is renal, so $^{11}$C-MCG, which is not bound to GCP II, is also included in the "blocked" kidney, and that $^{11}$C-MCG may be a substrate for other enzymes and nonspecific transporters present in kidney, although at much lower affinity. The kidney has urea and glutamate transporters (ref 16,17), each of which could be a target of $^{11}$C-MCG and may be blocked in a dose-dependant manner. If so, they may contribute significantly to the blockade depicted in FIG. 1. Further studies are necessary to uncover the GCP II—specific vs. transporter binding activity of $^{11}$C-MCG in the kidney.

$^{11}$C-MCG also displayed salutary metabolic characteristics for an enzyme-based radiopharmaceutical, i.e., little metabolism either in the plasma or in the target organ which is beneficial for certain applications in tracer kinetic modeling used for quantification of enzyme activity.

Figure 3A:
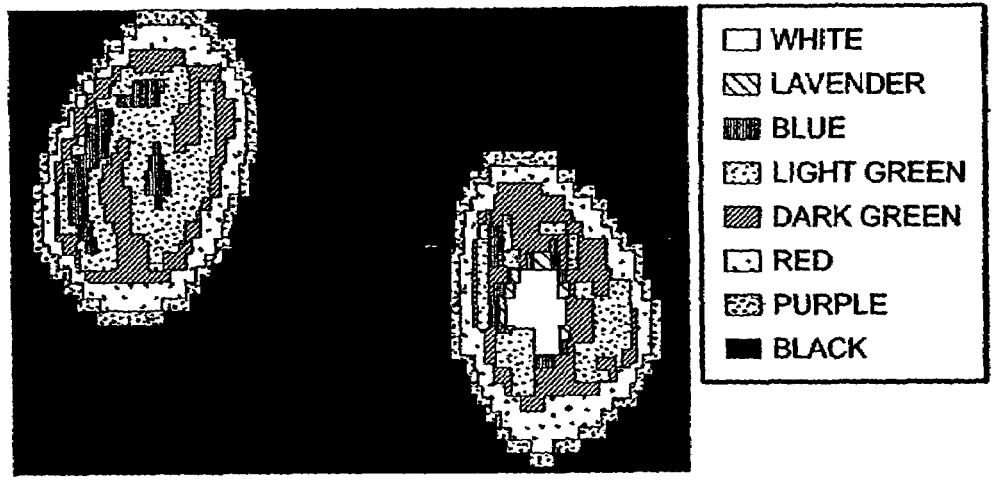
FIG. 3 is a series of photographs of a static baboon renal PET image obtained before (A) and after (B) administration of blocker (2 mg/kg PMPA). Note decrease in cortical radioactivity after blocker administration.
Figure 3B:
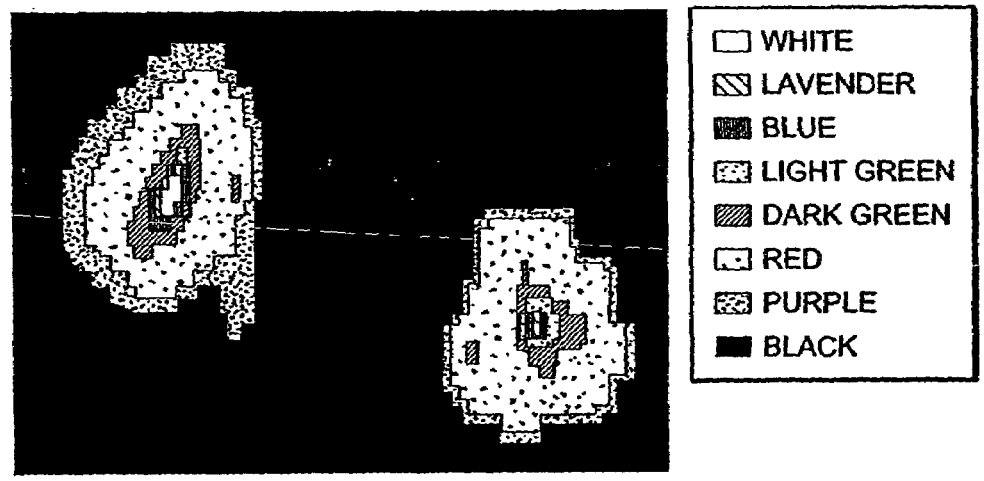

In one primate PET study with $^{11}$C-MCG, blocking of $^{11}$C-MCG uptake was demonstrated when the animal was pretreated with a low dose (2 mg/kg) of PMPA, a previously determined safe dose to administer to primates (FIG. 3). Because of renal excretion of $^{11}$C-MCG, less than complete blockade of radiotracer was demonstrated in the baboon renal cortex. Although concentration of GCP II has not been determined in the primate renal cortex and its relative concentration to that in the mouse kidney or to the prostate is unknown, GCP II activity is present in the human renal cortex. Little metabolism of the injected $^{11}$C-MCG was observed in primate plasma similar to the low metabolic rate of $^{11}$C-MCG seen in mouse plasma.

Brain uptake of $^{11}$C-MCG was low, suggesting that $^{11}$C-MCG, a preferred compound of the invention will have limited applicability as a probe of brain GCP II activity. That is due to its hydrophilicity (LogP=−0.235) and the lack of a suitable transport mechanism that is active within the time scale of a typical PET study (90 minutes). Other compounds of the invention including compounds of Formula I, Ia, II, III, and IV offer improved lipophilicity and may exhibit improved transport across the blood brain barrier such that these compounds may be suitable for use in imaging of the brain and the central nervous system.

EXAMPLES

The present invention is further illustrated by the following examples which should not be construed as limiting in any way. The contents of all cited references (including literature references, issued patents, published patent applications) as cited throughout this application are hereby expressly incorporated by reference. The practice of the present invention will employ, unless otherwise indicated, conventional techniques, which are within the skill of the art. Such techniques are explained fully in the literature.

General Chemistry

N,N-Dimethylformamide (DMF) was distilled under reduced pressure from barium oxide. High performance liquid chromatography (HPLC) equipment consisted of model 7126 injectors (Rheodyne, Rohnert, Calif.) model 590 EF pumps (Waters, Milford, Mass.), a model 440 ultraviolet (UV) absorbance detector (214 nm) (Waters), and a 5.08 cm (2 in.) NaI (T1) crystal scintillation detector (model 276, Ortec, Oak Ridge, Tenn.). Model 3390A integrators (Hewlett-Packard, Andover Mass.) and a Dynamax system (Rainin Instrument, Woburn Mass.) were used to record and analyze HPLC chromatograms. Semipreparative (10×250 mm) and analytical (4.6×250 mm) reverse-phase HPLC columns (C-18 Luna, Phenomenex, Torrance, Calif.) were used for purification and quality control, respectively, of the radiotracer.

Example 1

Synthesis of 2-[3-(1-Carboxy-2-$^{11}$C-methylsulfanyl-ethyl)-ureido]-pentanedioic acid Facile radiosynthesis of $^{11}$C-MCG was effected by treatment of the corresponding desmethyl precursor with $^{11}$C-iodomethane as depicted in Scheme 1. A carrier peak for $^{11}$C-MCG ($t_R$=3.9 min) was not readily detected at the 214 nm wavelength. The analytical HPLC conditions can detect MCG at 20 nmol. Based on that detection limit, a minimum specific radioactivity of $^{11}$C-MCG of 167 gBq/μmol (4000 Ci/mmol) at end of synthesis was derived. In all likelihood, specific radio-activites for $^{11}$C-MCG are much higher based on our extensive preparation of other $^{11}$C-methylated radiotracers under similar reaction conditions. Radiochemical yield based on starting $^{11}$C-iodomethane was calculated to be 16% (n=6) and radiochemical purity was >97%. The time of synthesis including formulation was approximately 30 minutes (from the end of bombardment).

Scheme 1:

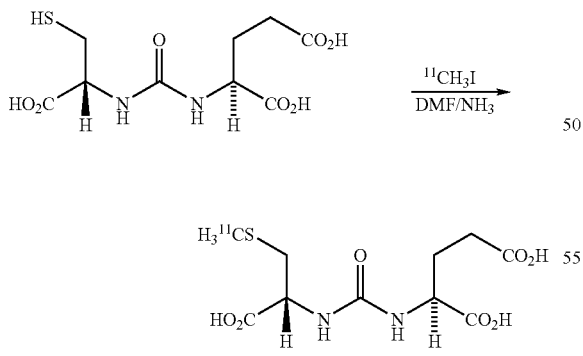

(2-[(2-Carboxy-3-mercapto-propyl)-hydroxy-phosphinoylmethyl]-pentanedioic acid (the S-desmethyl precursor of $^{11}$C-MCG; 1 mg) was dissolved in 0.1 mL of DMF To that solution was added 0.1 mL of a DMF/NH3 solution (freshly prepared by bubbling anhydrous ammonia at about 50 mL/min into 10 mL of DMF for 5 minutes) followed by 0.05 mL of water. The precursor solution, contained in a 1 mL spetum sealed vial, was cooled in a 20° C. bath and $^{11}$C-iodomethane prepared from a MeI MicroLab module (GE, Milwaukee, Wis.) and GE PET trace cyclotron was bubbled into the vial. The reaction vessel was subsequently heated in a 45° C. bath for 60 seconds before quenching the reaction with 0.6 mL of HPLC buffer (6/94/0.075 acetonitrile/water/trifluoroacetic acid) and 0.05 mL of 20% trifluoroacetic acid. The contents of the reaction vessel were injected onto a HPLC column using the above described HPLC buffer solution at a flow rate of 10 mL/min and UV detector at 214 nm. The radioproduct ($t_R$=8.1 min) was well separated from the thiol precursor ($t_R$=2.5 min) and was remotely collected. Rotary evaporation of the solvent (80° C. under vacuum) was followed by formulation of the radiotracer in 0.9% sterile saline (7 mL) and sterile filtration (Acro-disc 0.2 μm, 25 mm HT Tuffryin filter, PALL Gelman Laboratories, Ann Arbor, Mich.) into a 10 M1 sterile evacuated dose vial. For specific radioactivity determination, a 0.1 mL aliquot of $^{11}$C-MCG (typically approximately 3 mCi) was assayed for radioactivity and injected onto an analytical HPLC column using a mobile phase of 10/90 acetonitrile/0.01 M phosphoric acidat 2 mL/min. After determination of the specific radioactivity of $^{11}$C-MCG, 3 mL of 8.4% sterile, sodium bicarbonate was added to the radiotracer to bring the pH fo the final formulation to approximately 7. (Applicants have discovered that the addition of the bicarbonate solution prior to removal of an aliquot for specific radioactivity determination resulted in an undesired shortening of the retention time of the $^{11}$C-MCG and a noisier UV baseline.

Example 1a

Synthesis of Asymmetric Ureas Having A Phe-C(O)-Glu or Tyr-C(O)-Glu Scaffold

Asymmetric ureas according to Formula III or Formula IV may be prepared by transmetallation and fluorination as described in J. Chem. Soc. Chem. Comm. 1986 pg 1623. Typically, a trimethyltin or dimethylamine substituted aryl group is treated at room temperature with cesium sulfate in acetonitrile followed by addition of a source of fluorine. See for example Scheme 2.

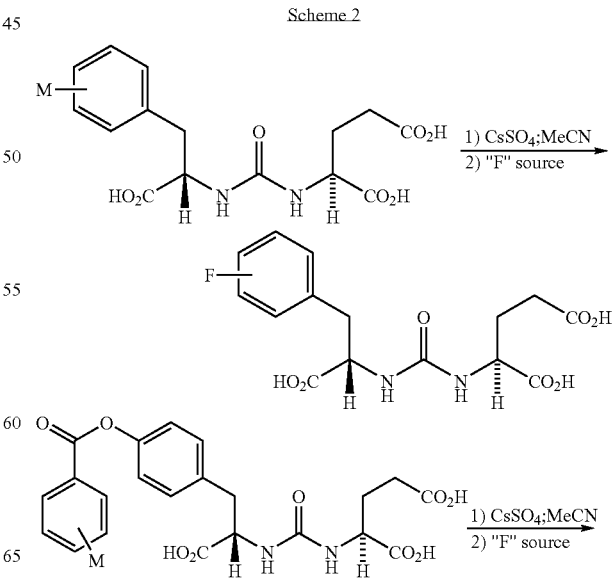

-continued

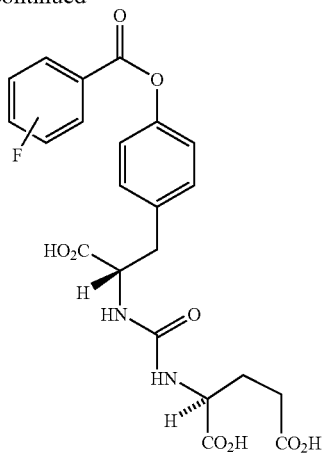

Example 2

Rodent In vivo Biodistribution Studies of $^{11}$C-MCG

All animals studies were approved by the Animal Care and Use Committee of the Johns Hopkins University.

Male CD-1 mice (Charles River, Wilmington, Mass.) weighing between 20 and 25 g were used and received an injection of 3.7 MBq (100 μCi) of $^{11}$C-MCG through the tail vein. That amounted to, at a maximum, 0.27 μg/kg. For kinetic studies, mice were killed by cervical dislocation at 5, 15, 30, 60, and 120 min after injection fo the radiotracer in 200 μL of saline vehicle. The brains were removed and placed on ice, and the cerebellum, olfactory bulb, hypothalamus, hippocampus, striatum, parietal cortex, brainstem, and thalamus were harvested. Kidneys, blood, fat, muscle, small intestine, and prostate were also harvested. The tissue samples were weighted, and their radioactivity content was determined in an automated γ counter (1282 Compugamma CS: Pharmacia/LKB Nuclear, Gaithersburg Md.). Aliquots of the injected tracer were counted along with the samples and served as standards for the calculation of percentage injected dose per gram of tissue (% ID/g). To assess binding specificity, groups of three mice each were pretreated with the high affinity GCP II inhibitor PMPA at does of 1, 10 and 100 mg/kg in 200 μL of saline vehicle 5 minutes prior to $^{11}$C-MCG injection. In an additional binding specificity study, animals were pretreated similarly with unlabeled MCG standard at doses of 5, 50, 100, 500, and 1000 μg/kg before $^{11}$C-MCG injection ANOVA, which was used in rodent radiotracer uptake studies, was performed with StatView SE Graphic software, version 1.03 (SAS Institute, Cary, N.C.). For the Students t test, $p<0.01$ was considered to indicate statistical significance.

Figure 2:
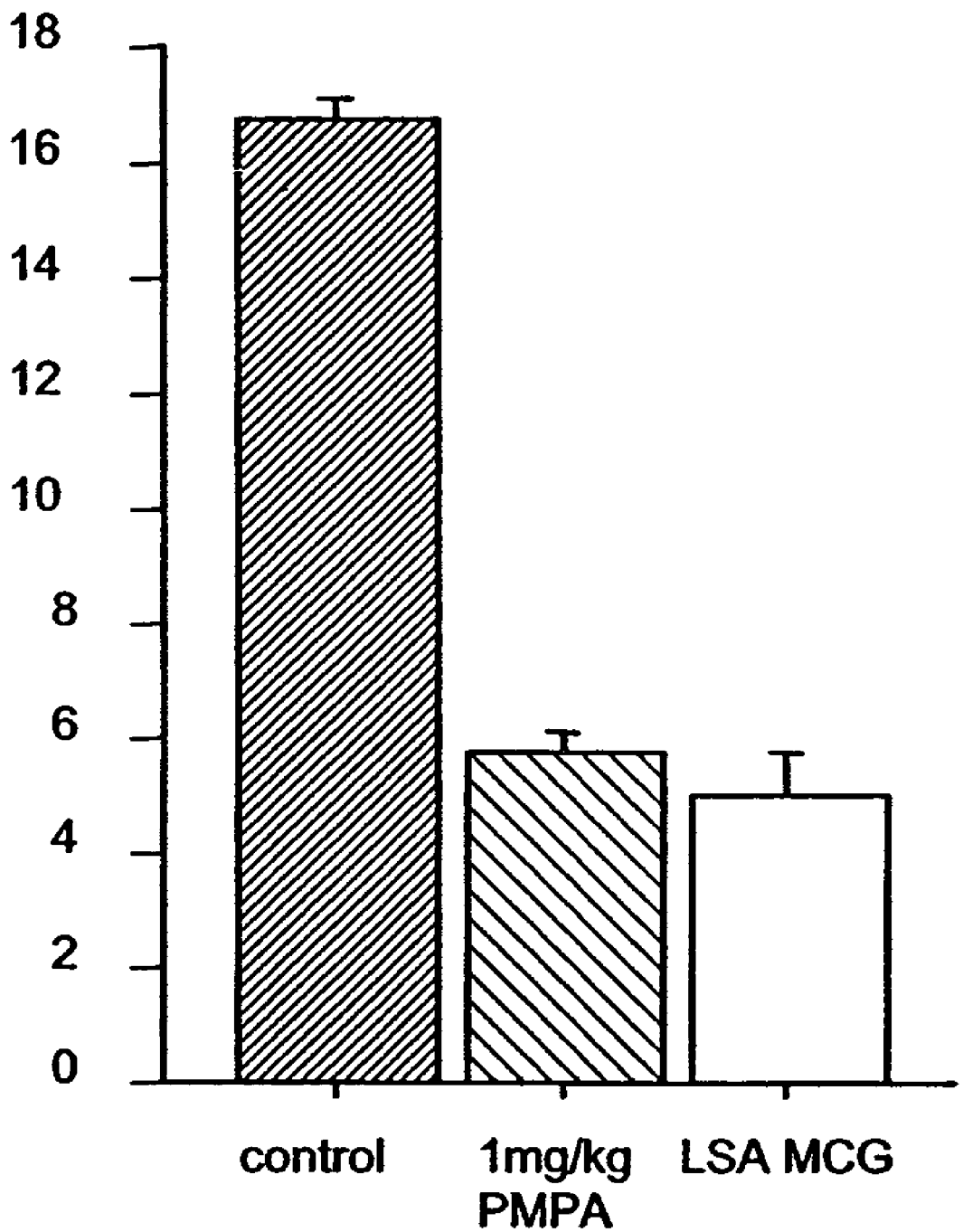
FIG. 2 is a table of the binding of $^{11}C$-MCG in the presence of various amounts of another high affinity inhibitor of GCP II (PMPA) Sacrifice time was 30 minutes in each experiment. LSA low specific activity. Statistical significance is indicated by an asterisk over the error bar (p<0.01).

Regional uptake at 5, 15, 30, 60, and 120 minutes for $^{11}$C-MCG in mous organs is presented in Table 1. Radiotracer concentration was highest in the target organ, the kidneys, and showed prompt washout, that is, within the time course of the study. Kidney/blood and kidney/muscle ratios were 30 and 73 respectively, at 30 minutes after injection. Prostate uptake was 1.55±1.01% ID/G at 30 minutes (n=3). Little activity gained access to the brain, with <0.1% ID/g in the cerebellum, hippocampus, or cortex and only 0.12±0.03% ID/g in the brainstem at 30 minutes post injection. FIG. 1 depicts the significant (inset $p<0.0001$ and $p=0.0002$ in the case of low-specific-activity (LSA) MCG and PMPA, respectively) blocking of radiotracer uptake when mice were pretreated with either an excess of unlabeled MCG (up to 1 mg/kg) or PMPA (1 mg/kg) (FIG. 2), indicating target binding specificity. An approximately sixfold reduction in uptake was demonstrated for either MCG or PMPA.

TABLE 1

Biodistribution of $^{11}$C-MCG in Male CD-1 Mice

| | % ID/g ± SD (N = 4) | | | | |
|---|---|---|---|---|---|
| Tissue | 5 min | 15 min | 30 min | 60 min | 120 min |
| Blood | 6.19 ± 0.94 | 3.27 ± 0.50 | 1.09 ± 0.22 | 0.25 ± 0.01 | 0.09 ± 0.03 |
| Heart | 2.43 ± 0.38 | 1.10 ± 0.10 | 0.38 ± 0.09 | 0.13 ± 0.00 | 0.07 ± 0.06 |
| Liver | 1.42 ± 0.20 | 0.87 ± 0.05 | 0.50 ± 0.00 | 0.30 ± 0.02 | 0.07 ± 0.03 |
| Kidneys | 60.94 ± 6.95 | 54.15 ± 3.69 | 32.99 ± 5.14 | 11.70 ± 1.99 | 0.22 ± 0.05 |
| Muscle | 2.23 ± 0.37 | 1.08 ± 0.48 | 0.45 ± 0.13 | 0.25 ± 0.22 | 0.09 ± 0.04 |
| Fat | 1.17 ± 0.93 | 0.75 ± 0.27 | 0.41 ± 0.16 | 0.12 ± 0.04 | 0.06 ± 0.05 |
| Small Intestine | 1.10 ± 0.41 | 0.70 ± 0.10 | 0.43 ± 0.12 | 0.23 ± 0.05 | 0.12 ± 0.02 |

Example 3

Metabolism Studies of $^{11}$C-MCG

At different times after injection of $^{11}$C-MCG into mice, blood and kidneys were collected to determine the rate of metabolism of the radiotracer. Heparinized blood (0.2-0.3 mL) was diluted to 0.9 mL with cold 0.9% saline and acidified to 0.5 N by the rapid addition of 0.1 mL of 5 N perchloric acid. Following 5 minutes on ice, the precipitate was removed by centrifugation to yield an acid-soluble supernatant that was analyzed by HPLC. Similarly, an acid extract of mouse kidney was obtained from an initial homogenate of two kidneys in 0.8 mL of cold water.

The acid extracts were loaded onto a 4.6×250 mm Prodigy ODS-3 column (Phenomenex) eluted with 10% acetonitrile in 50 mM sodium phosphate buffer pH 2.5 at a flow rate of 2 mL/min. Radioactivity was measured by a dual BGO flow detector and the chromatograph analyzed by Laura software (Bioscan, Washington, D.C.). $^{11}$C-MCG eluted after 4.0 minutes with a minor, earlier eluting product at 2.5 minutes.

Metabolites were determined in vivo at 5, 15, 30, and 60 minutes and showed at most 9.2% metabolism in plasma at 60 minutes (n=2) and 10.4% metabolism in kidney (n=2). The 30 minute time points (n=2) showed 3.5 5 and 2.0% metabolism for plasma and kidney, respectively.

Example 4

Baboon PET study of $^{11}$C-MCG

A dynamic PET study of the renal cortical uptake and clearance of $^{11}$C-MCG was performed in an adult male baboon (Papio anubis; body weight, approximately 30 kg). Before each study, two intraveneous catheters and a single arterial catheter were placed for infusion of anesthesia, injection of radiotracer and sampling of arterial blood, respectively. The animal was initially anestitized intramuscurally with 8-10 mg/kg alfadolone and alfaxalone acetate (Saffan; Pitman-Moore, Middlesex, UK) and was intubated. Anesthesia was maintained throughout the study by a continuous intravenous infusion drip of 6-9 mg/kg/h of Saffan. The animal was secured to the PET bed using an individually fitted thermoplastic mask. Pulse, blood pressure, and oxygen saturation were monitored continuously during the studies. Blood oxygen saturation was always maintained above 85%. After the animal was positioned in the PET scanner, transmission scanning was performed with a 370 MBq (10 mCi) [68]Ga source to allow for attenuation correction. PET scanning was started immediately after intravenous injection of 370 MBq (10 mCi) of high-specific-acitivtiy $^{11}$C-MCG (corresponding, at a maximum, to 0.02 µg/kg). Thirty-five simultaneous, contiguous (18 directed planes, 17 cross planes, z-axis 14.45 cm), sequential quantitative tomographic slices fo the brain were obtained with a GE Advance PET tomograph (General Electric Medical Systems, Milwaukee, Wis.) in the high-resolution mode (4.25-5.00 mm ful width at half maximum within the slice) over a 90 minute period. The animal was positioned so that the renal cortex was in the filed of view. Approximately 30 arterial blood samples (for radioassay and protein binding) were obtained over 90 minutes. To correct the input function for unmetabolized $^{11}$C-MCG, arterial samples were also obtained at 10, 20, 30, 45, 60, 75, and 90 minutes.

PET images were reconstructed from the raw data using a two-dimensional OSEM algorithm. Images were corrected for attemnuation and decay and were scaled to the same maximum. A region of interest was chosen over the left lower pole renal cortex and time-activity curves (TACs) were generated. To assess binding specificity, 2 mg/kg of PMPA (in 6 mL of saline) was administered intraveneously 10 minutes prior to injection of $^{11}$C-MCG at the end of the first 90 minute scan. Static images obtained over 10 minutes were performed before and after blocker. See FIG. 3.

Figure 4:
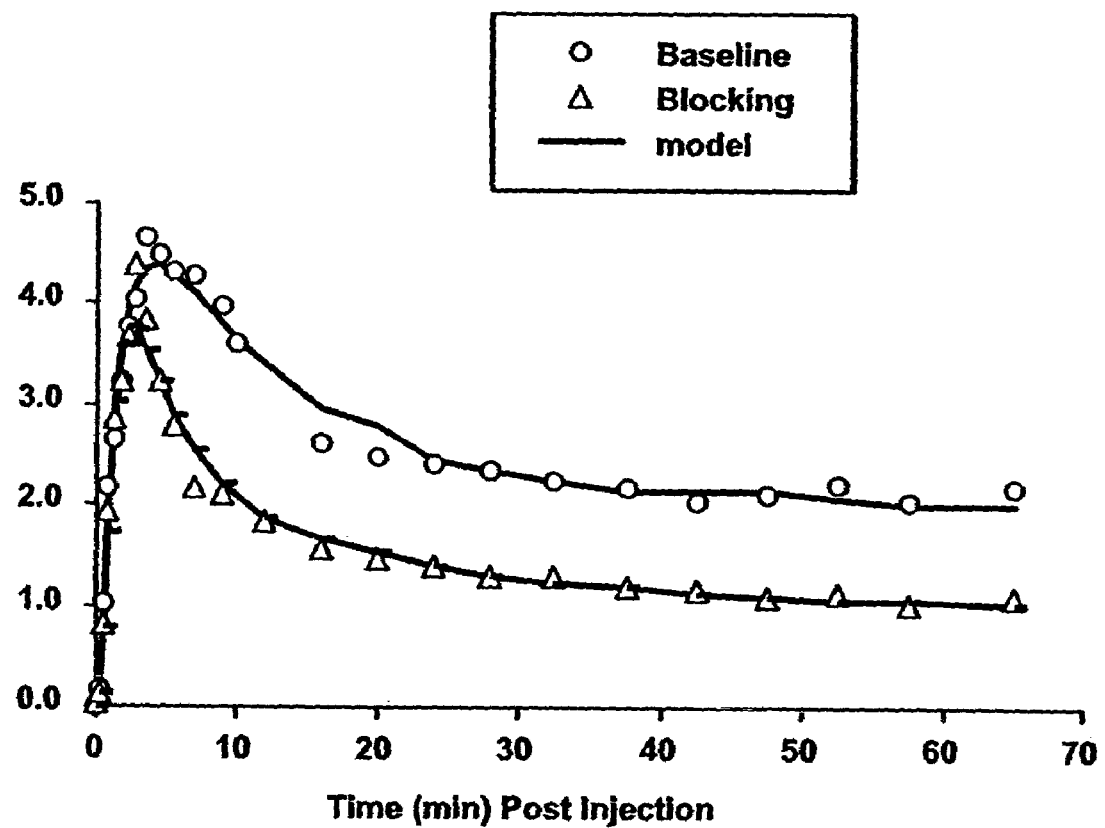
FIG. 4 is a plot of baboon renal TAC before and after blocker (2 mg/kg PMPA). Note the decrease in renal cortical radioactivity after administration of the blocker.

When $^{11}$C-MCG was administered to a male baboon, there was prominent uptake within the renal cortex, a peripheral site of GCP II in the primate (FIG. 3). Pretreatment of the animal with 3 mg/kg PMPA showed a decrease in renal cortical radiotracer uptake as demonstrated in FIG. 3, in the TACs (FIG. 4) and by a 37% reduction in the DV (from 1.38 to 0.878 mL/mL).

At baseline, peak metabolism of $^{11}$C-MCG was 9.0% at 90 minutes after injection. Administration of blocker (2 mg/kg PMPA), 10 minutes prior to tracer injection decreased $^{11}$C-MCG metabolism, which showed a peak value of 4.0% at 90 minutes post injection.

Example 5

Tracer Kinetic Modeling

A one-tissue, three parameter ($K_1$=influx, $k_2$ efflux, DV=distribution volume) model was applied to the TACs and to the metabolite-corrected renal uptake curves to describe tracer kinetics with DV ($=K_1/k_2$ in ml/ml) used as anindex of receptor density. The effect of blocking with PMPA was evaluated by changes in the Dva nd calculated as $100 \times (DV_{baseline} - DV_{blocker})/DV_{baseline}$. The model was fit to the PET data using nonlinear least squares minimization (ref 9)

The disclosures of all articles and references mentioned in this application, including patents, are incorporated herein by reference.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound according to Formula I

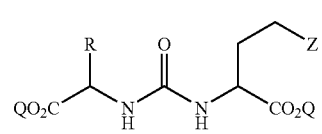

wherein

R is selected from the group consisting of fluoroalkyl, aryl, and benzyl, each of which is optionally substituted with an optionally substituted alkyl, optionally substituted alkenyl, optionally substituted alkynyl, optionally substituted aryl, optionally substituted alkanoyl, or optionally substituted aralkyl, optionally substituted alkoxy, optionally substituted aralkyloxy, or optionally substituted phenoxy, and wherein the R group comprises one or more positron emitting radioactive isotopes;

Q is hydrogen, optionally substituted alkyl, optionally substituted benzyl or optionally substituted phenyl; and Z is H, $CO_2H$; or a pharmaceutically acceptable salt thereof.

2. The compound of claim 1, wherein the R group comprises one or more isotopes selected from $^{11}$C, $^{18}$F, $^{99}$Tc, $^{123}$I or any combination thereof.

3. The compound of claim 1, wherein the compound is according to Formula Ia:

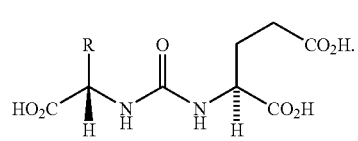

4. A compound according to Formula II

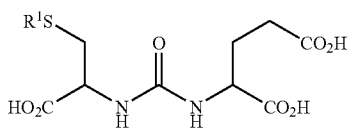

II wherein $R^1$ is selected from methyl, optionally substituted alkenyl, optionally substituted alkynyl, optionally substituted fluoroalkyl, optionally substituted aryl, and optionally substituted aralkyl, and the $R^1$ group comprises at least one radioactive isotope or fluorescent dye selected from $^{11}C$, $^{18}F$, $^{99}Tc$, $^{123}I$, or any combination thereof; or a pharmaceutically acceptable salt thereof.

5. The compound of claim 4, wherein $R^1$ is selected from the group consisting of $^{11}C$-methyl, optionally substituted $C_{1-6}$alkyl, optionally substituted $C_{7-12}$ aralkyl, and optionally substituted $C_{6-12}$aryl, each of which are substituted with one or more $^{11}C$-methyl groups, $^{18}F$, $^{99}Tc$, $^{123}I$, $^{125}I$, $^{131}I$, or a combination thereof.

6. The compound of claim 5, wherein $R^1$ is $^{11}C$-methyl, $C_{1-6}$alkyl substituted with one or more $^{18}F$, or benzyl substituted with one or more $^{18}F$.

7. The compound of claim 1, wherein the compound is according to Formula III:

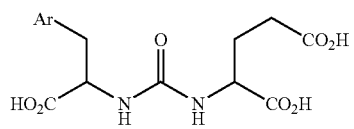

III wherein Ar is a carbocyclic aromatic group having from 6 to about 18 carbon atoms and between 1 and about 3 rings which is substituted with one or more groups selected from halogen, alkyl, amino, hydroxy, optionally substituted alkyl, optionally substituted alkenyl, optionally substituted alkynyl, optionally substituted benzoyloxy, and optionally substituted alkoxy, and wherein Ar comprises one or more positron emitting isotopes; or a pharmaceutically acceptable salt thereof.

8. The compound of claim 7, wherein the compound is according to Formula IV:

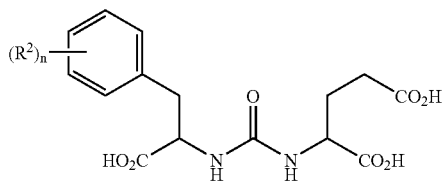

IV wherein $R^2$ is selected from the group consisting of fluoro, chloro, bromo, iodo, hydroxy, amino, mono and di alkylamino, optionally substituted alkyl, optionally substituted alkenyl, optionally substituted alkynyl, optionally substituted fluoroalkyl, optionally substituted aryl, optionally substituted benzoyloxy, and optionally substituted alkoxy wherein $R^2$, or the phenyl group to which $R^2$ is bound, comprises one or more positron emitting isotopes; and n is an integer from 1 to 5.

9. The compound of claim 7, wherein Ar comprises one or more positron emitting isotopes of $^{11}C$, $^{18}F$, $^{99}Tc$, $^{123}I$ or any combination thereof.

10. The compound of claim 8, wherein $R^2$ is selected from the group consisting of $^{11}C$-methyl, $^{11}C$-methoxy, optionally substituted $C_{1-6}$alkyl, optionally substituted $C_{7-12}$aralkyl, and optionally substituted $C_{6-12}$aryl, each of which are substituted with one or more $^{11}C$-methyl groups, $^{18}F$, $^{99}Tc$, $^{123}I$, $^{125}I$, $^{131}I$, or a combination thereof.

11. The compound of claim 8, wherein $R^2$ is phenyl substituted with one or more groups selected from hydroxy, $^{11}C$-methoxy, $^{11}C$-methyl, $^{18}F$, $^{123}I$ and benzoyloxy which may be substituted with one or more fluoro groups, or a combination thereof.

12. A pharmaceutical composition comprising a pharmaceutically acceptable carrier and a compound or salt of claim 1.

13. A package comprising a pharmaceutical composition of claim 12 in a container and further comprising indicia comprising at least one of:
   instructions for using the composition to image cells or tissues expressing at least one of NAALADase or PSMA, or
   instructions for using the composition to image glutamatergic neurotransmission in a patient suffering from a stress-related disorder, or
   instructions for using the composition to image prostate cancer.

14. A compound which is 2-[3-(1-Carboxy-2-$^{11}C$-methylsulfanyl-ethyl)-ureido]-pentanedioic acid.

15. The compound of claim 1, wherein the compound is according to Formula V:

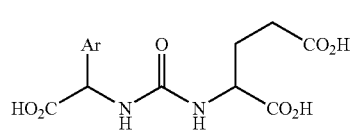

V wherein Ar is a carbocyclic aromatic group having from 6 to about 18 carbon atoms and between 1 and about 3 rings which is substituted with one or more groups selected from halogen, alkyl, amino, hydroxy, optionally substituted alkyl, optionally substituted alkenyl, optionally substituted alkynyl, optionally substituted benzoyloxy, and optionally substituted alkoxy, and Ar comprises one or more positron emitting isotopes; or a pharmaceutically acceptable salt thereof.

16. The compound of claim 15, wherein the compound is according to Formula VI:

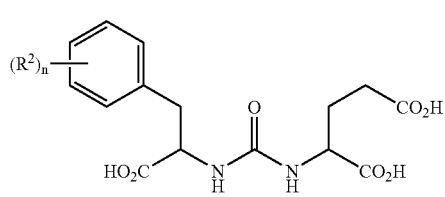

VI wherein $R^2$ is selected from the group consisting of fluoro, chloro, bromo, iodo, hydroxy, amino, mono and di alkylamino, optionally substituted alkyl, optionally substituted alkenyl, optionally substituted alkynyl, optionally substituted fluoroalkyl, optionally substituted aryl, optionally substituted benzoyloxy, and optionally substituted alkoxy wherein $R^2$, or the phenyl group to which $R^2$ is bound, comprises one or more positron emitting isotopes; and n is an integer from 1 to 5.

17. The compound of claim 15, wherein Ar comprises one or more positron emitting isotopes of $^{11}C$, $^{18}F$, $^{99}Tc$, $^{123}I$ or any combination thereof.

18. The compound of claim 16, wherein $R^2$ is selected from the group consisting of $^{11}C$-methyl, $^{11}C$-methoxy, optionally substituted $C_{1-6}$alkyl, optionally substituted $C_{7-12}$aralkyl, optionally substituted $C_{6-12}$aryl, each of which are substituted with one or more $^{11}C$-methyl groups, $^{18}F$, $^{99}Tc$, $^{123}I$, $^{125}I$, $^{131}I$, or a combination thereof.

19. The compound of claim 16, wherein $R^2$ is phenyl substituted with one or more groups selected from hydroxy, $^{11}C$-methoxy, $^{11}C$-methyl, $^{18}F$, $^{123}I$, and benzoyloxy which may be substituted with one or more fluoro groups, or a combination thereof.

20. A compound according to Formula VII:

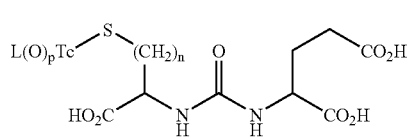

wherein

L is a chelating ligand suitable for coordination to Tc;
p is 0, or 1; and
n is an integer of from 1 to 6; or a pharmaceutically acceptable salt thereof.

21. The compound of claim 20, wherein the compound is according to Formula VIII:

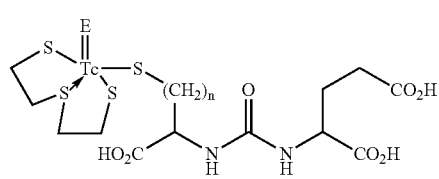

where E is oxygen or absent.

22. The compound of claim 8, wherein the compound is according to Formula IX:

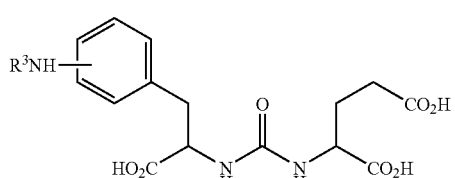

wherein $R^3$ is a fluorescent dye which emits in the visible or near infrared spectrum.

23. The compound of claim 22, wherein $R^3$ is FITC, a derivative thereof, carbocyanine, or a derivative thereof.

24. The compound of claim 1, wherein the compound is selected from the group consisting of:

2-[3-(1-Carboxy-3-11C-methylsulfanyl-propyl)-ureido]-pentanedioic acid,

2-[3-(1-Methoxycarbonyl-3-$^{11}C$-methylsulfanyl-propyl)-ureido]-pentanedioic acid, 2-[3-(1-Carboxy-2-$^{11}C$-methylsulfanyl-ethyl)-ureido]-4-(1H-tetrazol-5-yl)-butyric acid and, 2-{3-[Carboxy-(4-$^{11}C$-methoxy-phenyl)-methyl]-ureido}-pentanedioic acid.

25. A package comprising:
(i) a compound of the following Formula I:

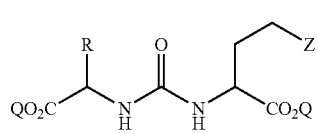

wherein

R is selected from the group consisting of fluoroalkyl, aryl, and benzyl, each of which is optionally substituted with an optionally substituted alkyl, optionally substituted alkenyl, optionally substituted alkynyl, optionally substituted aryl, optionally substituted alkanoyl, or optionally substituted aralkyl, optionally substituted alkoxy, optionally substituted aralkyloxy, or optionally substituted phenoxy, and wherein R comprises one or more positron emitting radioactive isotopes;

Q is hydrogen, optionally substituted alkyl, optionally substituted benzyl or optionally substituted phenyl; and Z is H, $CO_2H$; or a pharmaceutically acceptable salt thereof;

and (ii) indicia comprising at least one of:

instructions for using the composition to image cells or tissues expressing at least one of NAALADase or PSMA, or instructions for using the composition to image glutamatergic neurotransmission in a patient suffering from a stress-related disorder, or instructions for using the composition to image prostate cancer.

26. A package of claim 25 wherein the package comprises instructions for using the composition to image cells or tissues expressing at least one of NAALADase or PSMA.

27. A package of claim 25 wherein the package comprises instructions for using the composition to image glutamatergic neurotransmission in a patient suffering from a stress-related disorder.

28. A package of claim 25 wherein the package comprises instructions for using the composition to image prostate cancer.

* * * * *